US00PP09426P

United States Patent [19]

Bak et al.

[11] Patent Number: Plant 9,426

[45] Date of Patent: Jan. 9, 1996

[54] GUZMANIA PLANT NAMED TORCH

[75] Inventors: Gerardus J. Bak, Assendelft; Nicholaas D. Steur, Oude Niedorp; Elly Bak, Rijsenhout, all of Netherlands

[73] Assignee: Corn Bak B.V., Assendelft, Netherlands

[21] Appl. No.: 366,607

[22] Filed: Dec. 29, 1994

[51] Int. Cl.[6] ..... A01H 5/00

[52] U.S. Cl. ..... Plt./88.8

[58] Field of Search ..... Plt./88.8

*Primary Examiner*—James R. Feyrer

*Attorney, Agent, or Firm*—Foley & Lardner

[57] ABSTRACT

A new cultivar of Guzmania named 'Torch' characterized by an inflorescence on a stalk measuring approximately 6 cm in height as flowering commences to approximately 18 cm in height at maturity; bright red (RHS 44A) primary bracts and yellow (RHS 14A) primary bract-ends produced on a strong, solid, compact, broad-leafed plant.

3 Drawing Sheets

The present invention relates to a new and distinct cultivar of Guzmania that is an interspecific hybrid, hereinafter referred to by the cultivar name 'Torch.'

Guzmania are predominantly epiphytic with a few terrestrial species and are native to the tropics. For the most part species vary in diameter from 7 or 8 inches to 3 or 4 feet and have rosettes of glossy, smooth edged leaves.

Floral bracts of Guzmania frequently have brilliant colors and may last for many months. The range of colors for Guzmania is generally from yellow through orange but may also include flame red and red-purple. White or yellow, tubular, three petalled flowers may also appear on a stem or within the leaf rosette but are usually short lived.

Guzmania may be advantageously grown as pot plants for greenhouse or home use. Desirably the plants are shaded from direct sunlight and during the spring to autumn period the central vase-like part of the leaf rosette is desirably filled with water.

Guzmania is native to tropical America. Leaves of Guzmania are usually formed as basal rosettes which are stiff and entire and in several vertical ranks. Guzmania have terminal spikes or panicles which are often bracted with petals united in a tube about as long as the calyx. The ovary is superior and the seeds plumose.

Asexual propagation of Guzmania is frequently done through the use of tissue culture practices. Propagation can also be from off-shoots produced by the plant which may then be rooted. The resulting plantlets are detached from the mother plant and may be potted up in a suitable growing mixture.

The new cultivar 'Torch' is a product of a planned breeding program and was originated by the inventors from a cross made during such a program in Assendelft, The Netherlands, in 1983. The male or pollen parent was a selection of *Guzmania conifera* identified by Code No. 839301. The female or seed parent was a selection of *Guzmania lingulata* identified by Code No. 839379. The selection comprising the new variety flowered for the first time in 1986 in Assendelft, The Netherlands. The selection was asexually propagated through off-shoots until 1988 when asexual propagation by tissue culture commenced. Continuous asexual propagation has demonstrated that the combination of characteristics as herein disclosed for the new cultivar 'Torch' are firmly fixed and are retained through successive generations of asexual reproduction.

'Torch' is particularly characterized by the following:

1. Solid compact growth habit in a funnel form rosette measuring 42–48 cm high when flowering.
2. Relatively wide leaves of 4 to 6 cm.

3. Superior floral bract production.
4. Large inflorescence on a stalk measuring from 6 cm high as flowering commences to approximately 18 cm high at maturity.
5. Long lasting habit.

'Torch' has not been tested under all available environmental conditions and the phenotype may vary with variations in environmental conditions such as temperature, light intensity, day length and humidity without a change in the genotype of the plant variety.

The accompanying color photographic drawings show typical characteristics of 'Torch', with colors being as true as possible with illustrations of this type.

Sheet 1 comprises a perspective view of a full plant with floral bracts.

Sheet 2 is also a perspective view of 'Torch' but showing the inflorescence at three different stages of development. Plants increasing in maturity are shown from right to left in the photograph.

Sheet 3 is a close-up of the inflorescence showing an individual petal that sometimes is disposed outside the bract.

In the following description, color references are made to The Royal Horticultural Society color chart (RHS).

The following traits have been repeatedly observed and in combination distinguish 'Torch' as a new and distinct cultivar. These observations, measurements and descriptions have been performed under greenhouse conditions in Assendelft, The Netherlands.

Plant:

*Form.*—Funnel form rosette.

*Height.*—Approximately 42–48 cm high when flowering.

*Growth habit.*—Stemless.

*Diameter.*—Approximately 50–60 cm.

Foliage:

*Size of leaf.*—Length — approximately 30 42cm long. Width — approximately 4–6 cm.

*Shape of leaf.*—Linear — lanceolate.

*Surface texture.*—Smooth.

*Variegation.*—None.

*Color.*—Upperside, RHS 137A–147A; underside, RHS 146A. The color of the leaves can vary depending on amount of fertilizer used.

*Number.*—Average number of leaves per plant at maturity approximately 20 to 26.

Bracts:

*Length.*—The lowest scape bracts are approximately 22 cm long. The bracts just below the primary bracts are approximately 8 cm long. The primary bracts are approximately 7 cm long. The lowest floral bracts are 7 to 8 cm long while the floral bracts near the top are approximately 4 cm long.

*Width.*—The scape bracts are approximately 4 cm wide, the primary bracts are approximately 4 cm wide and the floral bracts are approximately 1.5 cm wide.

*Number.*—There are approximately 14–18 scape bracts and the highest scape bracts (approximately 8) join the primary bracts in making a full inflorescence. There are approximately 8–10, primary bracts and 80 to 100 floral bracts.

*General shape.*—Lanceolate.

*Texture.*—Smooth.

*Margin.*—Entire.

*Color.*—The lowest scape bracts are RHS 137A — 147A. The middle part of the other scape bracts is RHS 44A with bracts-ends that are a mix of RHS 44A and 137A-147A. The primary bract-ends are RHS 14A.

Flowers:

*Borne (stalks).*—Erect.

*Shape of inflorescence.*—Head.

*Size of inflorescence on stalk.*—The size of the inflorescence changes with maturity measuring approximately 6 cm in height as flowering commences and approximately 18 cm in height at the end of flowering.

*Diameter of inflorescence.*—Approximately 7–9 cm.

*Individual petals.*—Generally disposed within the bracts. (1) Length: approximately 5 cm. (2) Width: approximately 0.5 cm. (3) Quantity: approximately 80 flowers. (4) Color: RHS 12A.

*Time of blooming.*—A fully grown plant can bloom the whole year starting ±16 weeks after natural induction or through treatment with acetylene.

*Duration of blooms.*—Each flower blooms one day and the total blooming period is about 10–13 weeks.

Reproductive organs

*Ovaries.*—Superior.

*Stamens.*—6 in number.

*Seed characteristics.*—Sterile hybrid therefore no fruit or seed.

We claim:

1. A new and distinct cultivar of Guzmania plant named 'Torch', as illustrated and described.

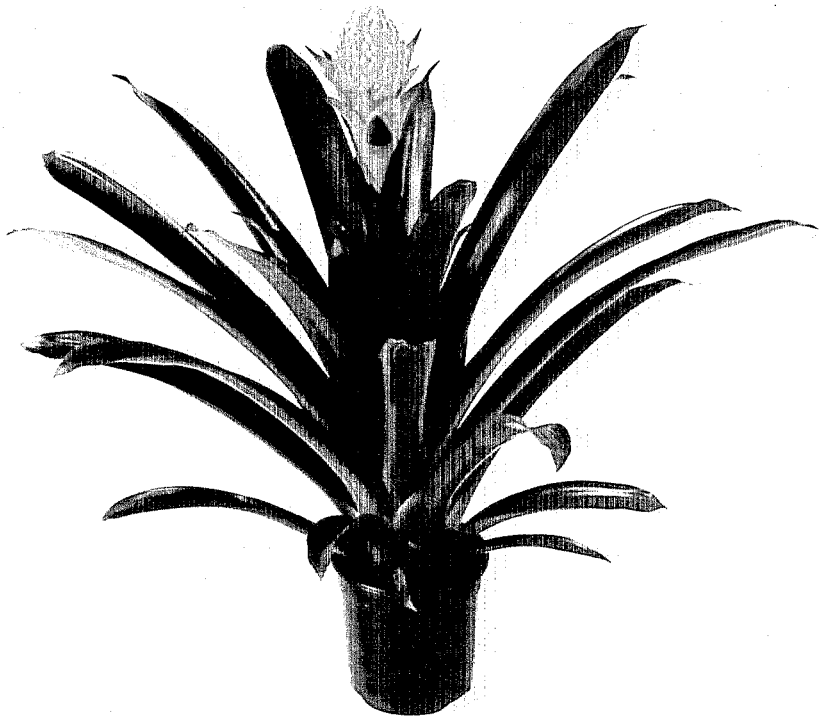

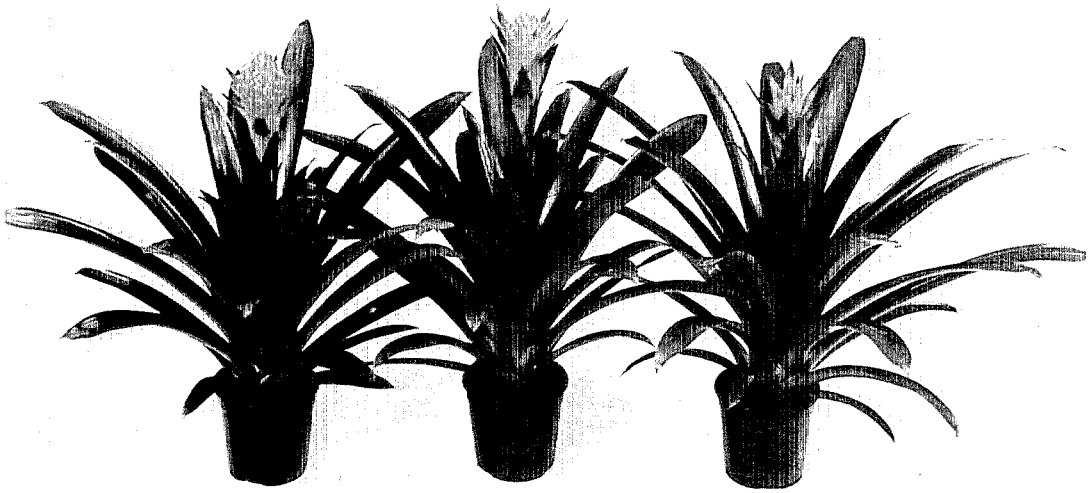

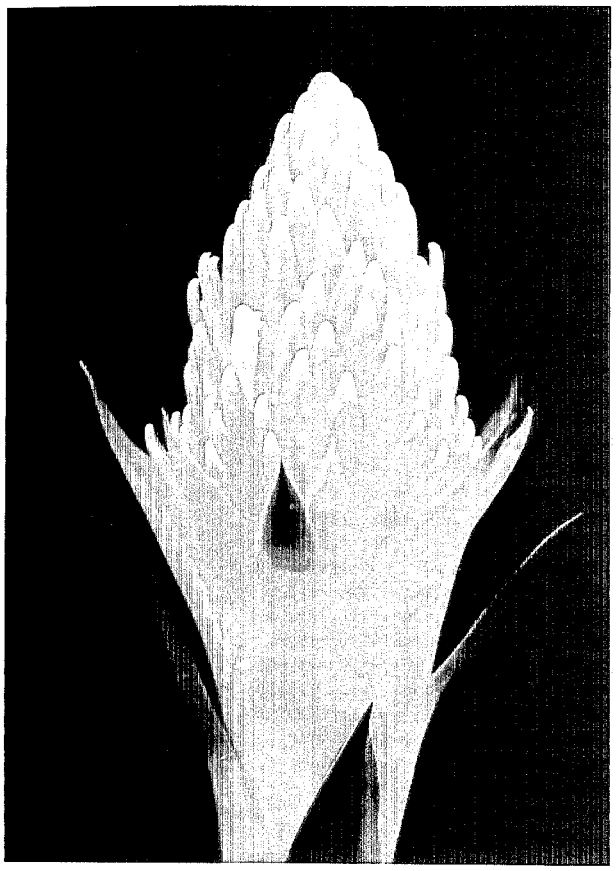

* * * * *